United States Patent [19]

Mitra

[11] Patent Number: 4,496,689

[45] Date of Patent: Jan. 29, 1985

[54] COVALENTLY ATTACHED COMPLEX OF ALPHA-1-PROTEINASE INHIBITOR WITH A WATER SOLUBLE POLYMER

[75] Inventor: Gautam Mitra, Kensington, Calif.

[73] Assignee: Miles Laboratories, Inc., Elkhart, Ind.

[21] Appl. No.: 565,810

[22] Filed: Dec. 27, 1983

[51] Int. Cl.$^3$ ............................................. C07G 7/00
[52] U.S. Cl. ............................... 525/54.1; 260/112 B; 260/112 R; 424/101; 514/59; 514/826; 435/174; 435/178; 435/179; 435/180; 435/181
[58] Field of Search ........ 260/112 R, 112 B, 112.5 R; 525/54.1; 424/177, 180, 183, 101; 435/174, 177, 178, 179, 180, 181

[56] References Cited

U.S. PATENT DOCUMENTS

| | | | |
|---|---|---|---|
| 3,788,948 | 1/1974 | Kagedal et al. | 525/54.1 |
| 3,947,352 | 3/1976 | Cuatrecasas et al. | 525/54.1 |
| 4,367,309 | 1/1983 | Kondo et al. | 525/54.1 |
| 4,379,087 | 4/1983 | Coan et al. | 260/112 B |
| 4,439,358 | 3/1984 | Coan et al. | 260/112 B |

OTHER PUBLICATIONS

Pannell et al., Biochemistry, 13, 5439 (1979).
Johnson et al., Biochem. Biophys. Res. Commun., 72, 33 (1976).
DelMar et al., Biochem. Biophys. Res. Commun., 88, 346 (1979).
Heimburger et al., Proc. Int. Res. Conf. Proteinase Inhibitors, 1st, 1–27 (1970).
Saklatavala et al., Biochem. J., 157, 339 (1976).
Musiani et al., Biochemistry, 15, 798 (1976).
Kress et al., Preparative Biochemistry, 3 (6), 541 (1973).
Glaser et al., Preparative Biochemistry, 5 (4), 333 (1975).
Hau et al., Proceedings of the International Workshop on Technology for Protein Separation and Improvement of Blood Plasma Fractionation, 1977, Reston, Va.
Marshall and Rabinowitz, Arch. Biochem. Biophys., 167, 777 (1975).
Marshall and Rabinowitz, J. Biol. Chem., 251, 1081 (1976).
Vegarud et al., Biotechnol. Bioeng., 17, 1391 (1975).
Christensen et al., Process Biochemistry, 25 (Jul/Aug 1976).
Chaplain et al., Biotech Bioeng., 24, 2627 (1982).
Tam et al., Proc. Natl. Acad. Sci., 73 (6), 2128 (1976).
Huylaerts et al., Thromb. Haemostas. (Stuttgart), 49 (2), 109 (1983).
Ceustermans et al., J. Biol. Chem., 257 (7), 3401 (1982).
Bjork et al., FEBS Letters, 143 (1), 96 (1982).
Abuchowski et al., J. Biol. Chem., 252 (11), 3578 and 3582 (1972).
Ashihara et al., Biochem. Biophys. Res. Commun., 83 (2), 385 (1978).
Koide et al., FEBS Letters, 143 (1), 73 (1982).
O'Neill et al., Biotechnol. Bioeng., 13, 319 (1971).

*Primary Examiner*—Lester L. Lee
*Assistant Examiner*—Nathan M. Nutter
*Attorney, Agent, or Firm*—Lester E. Johnson

[57] ABSTRACT

There is disclosed a process for producing a covalently attached alpha-1-proteinase inhibitor - water soluble polymer complex useful for pulmonary emphysema therapy, a covalently attached alpha-1-proteinase inhibitor - water soluble polymer complex produced by the process, a composition thereof in a pharmaceutically acceptable carrier, and a method for treating pulmonary emphysema by administering to a human patient a therapeutically effective amount of the complex or preparation.

45 Claims, 3 Drawing Figures

FIG. 1

Effects of heating (60°C) on EIC.

○ Native $\alpha_1$PI
▲ 0.117 moles Dextran/mole $\alpha_1$PI
● 0.585 moles Dextran/mole $\alpha_1$PI

FIG. 3

HPLC scan of native $\alpha_1$PI, bovine liver catalase $\alpha_1$PI-dextran and $\alpha_1$PI-dextran-catalase.

COVALENTLY ATTACHED COMPLEX OF ALPHA-1-PROTEINASE INHIBITOR WITH A WATER SOLUBLE POLYMER

BACKGROUND OF THE INVENTION

1. Field of the Invention

This invention relates to a chemical agent useful in the treatment of pulmonary emphysema. More particularly, this invention relates to a covalent complex (or conjugate) of a water soluble polymer which may be a polysaccharide or a polyol with human alpha-l-proteinase inhibitor, to a process for producing the covalent complex (or conjugate) of a polysaccharide or a polyol with alpha-l-proteinase inhibitor, optionally in the presence of catalase enzyme, to a pharmaceutical preparation comprising the covalent complex (or conjugate) of a polysaccharide or a polyol with alpha-l-proteinase inhibitor, and to a method for treating pulmonary emphysema comprising administering to a human patient a therapeutically effective amount of the complex (or conjugate) or pharmaceutical preparation according to the invention.

Alpha-l-proteinase inhibitor (abbreviated "$\alpha_1 PI$") is a glycoprotein having a molecular weight of 53,000 determined by sedimentation equilibrium centrifugation. The glycoprotein consists of a single polypeptide chain to which several oligosaccharide units are covalently bonded. Human alpha-l-proteinase inhibitor has a role in controlling tissue destruction by endogenous serine proteinases. A genetic deficiency of alpha-l-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-l-proteinase inhibitor inhibits human pancreatic and leukocyte elastases. See Pannell et al, *Biochemistry*, 13, 5339 (1974); Johnson et al, *Biochem. Biophys. Res. Commun.*, 72, 33 (1976); Del Mar et al, *Biochem, Biophys. Res. Commun.*, 88, 346 (1979); and Heimburger et al, *Proc. Int. Res. Conf. Proteinase Inhibitors*, 1st, 1–21 (1970).

2. Description of the Prior Art

Coan et al, U.S. Pat. No. 4,379,087, disclose a method for separating alpha-l-proteinase inhibitor from blood plasma or blood plasma fractions which contain the proteinase inhibitor. An aqueous solution of the blood plasma fraction is held at a pH of about 6.5–8.5 and at a temperature of about 2°–50° C., and for a period of about 0.2–24 hours and then mixed with a polycondensed polyglycol (e.g. polyethylene glycol) in the proportion of about 10–15 grams of polyglycol per 100 ml of aqueous solution containing the blood plasma fraction. The mixture may be held at temperature of about 2°–10° C. for a period of about 1–24 hours. Next, the pH of the mixture is adjusted to about 4.6–5.7 to selectively precipitate unwanted proteins from the solution without precipitation of alpha-l-proteinase inhibitor. Finally, alpha-l-proteinase inhibitor is separated from solution and purified further.

Other processes for the production of alpha-l-proteinase inhibitor have been reported. Pannell et al, *Biochemistry*, 13, 5439 (1974), mentioned above, disclose a process wherein albumin-poor blood plasma was pooled and fractionated with solid ammonium sulfate. The resulting precipitate was purified in a four-step procedure involving albumin removal using a Sepharose-Blue Dextran adsorption column, ammonium sulfate fractionation of the most active fractions from the first step, and two DEAE-cellulose chromatography separations.

Saklatvala et al, *Biochem. J.*, 157, 339 (1976) disclose a process to obtain alpha-l-proteinase inhibitor by fractionating human plasma using ammonium sulfate and chromatographing the resulting precipitate on DEAE-cellulose. The 0.5M NaCl extract therefrom was applied to a concanavalin A-Sepharose column and eluted with alpha-D-methyl glucopyranoside. The eluate was again applied to a DEAE-cellulose column and an eluate containing alpha-l-proteinase inhibitor was obtained using 0.0–0.2M NaCl.

Musiani et al, *Biochemistry*, 15, 798 (1976) disclose the use of 50% aqueous ammonium sulfate to separate an alpha-l-proteinase inhibitor from blood plasma which was solubilized and subjected to successive chromatographic separations using DEAE in exchanger, concanavalin A-Sepharose, Sephadex G-100 and an immuno adsorbent columns to yield purified alpha-l-proteinase inhibitor.

Kress et al, *Preparative Biochemistry*, 3 (6), 541 (1973), disclose the large scale purification of alpha-l-proteinase inhibitor from human plasma using 80% ammonium sulfate aqueous solution, the precipitate from which treatment was solubilized, dialyzed and chromatographed on DEAE-cellulose. The resulting concentrate was again dialyzed and gel-filtered on Sephadex G-100 and the alpha-l-proteinase inhibitor containing fractions were chromatographed twice on DE-52 cellulose.

Glaser et al, *Preparative Biochemistry*, 5 (4), 333 (1975), isolated alpha-l-proteinase inhibitor from Cohn Fraction IV-1 in 30% overall yield by chromatographing the Cohn Fraction IV-1 on DEAE-cellulose, QAE-Sephadex, concanavalin A-Sepharose and Sephadex G-150.

Hao et al, *Proceedings of the International Workshop on Technology for Protein Separation and Improvement of Blood Plasma Fractionation*, 1977, Reston, Virginia, disclosed an integrated plasma fractionation system based on the use of polyethylene glycol (PEG) to obtain proteins distributed in four PEG fractions using 0–4% PEG, 4–10% PEG, 10–20% PEG and 20% PEG. Alpha-l-proteinase inhibitor was among the several proteins isolated in the 20% PEG fraction.

Stabilization and modification of enzymes and other proteins by covalent attachment to carbohydrates and polyethylene glycol has been reported. Marshall and Rabinowitz, *Arch. Biochem. Biophys.*, 167, 77 (1975) and *J. Biol. Chem.*, 251, 1081 (1976), noting earlier reports that glycoproteins (mostly enzymes) often show unusual stability characteristics compared with carbohydrate-free proteins, the former being less sensitive to heat and other denaturing conditions and more resistant to proteolysis, disclose the preparation of soluble enzyme-carbohydrate conjugates by coupling (by means of covalent attachment) trypsin, $\alpha$-amylase and $\beta$-amylase to cyanogen bromide activated dextran. The resulting covalent conjugates displayed marked resistance to heat inactivation and denaturation, increased half-life, and reduction in loss of activity under conditions favoring antolysis.

Vegarud et al, *Biotechnol. Bioeng.*, 17, 1391 (1975) and Christensen et al, *Process Biochemistry*, 25 (July/August 1976), report the results of experiments carried out with "natural" glycoproteins as well as the "artificial" protein-glycoconjugates (produced by the cyanogen bromide method which have shown that glycosated enzymes are more stable towards heat inactivation by heat and proteases than the corresponding non-glycosated preparations.

Chaplin et al, *Biotech. Bioeng.*, XXIV, 2627 (1982), disclose soluble conjugates of pepsin and carboxypeptidase A prepared by covalent linkage of the enzyme to an amino derivative of dextran having specific activities close to those of the native enzymes and having increased temperature and pH stabilities.

Tam et al, *Proc. Natl. Acad. Sci.*, 73 (6), 2128 (1976), disclose a complex between soluble dextran and human hemoglobin, produced by two alternative methods involving cyanogen bromide (alkylation) and dialdehyde coupling chemistry, which is cleared through the kidneys and removed from circulation much more slowly than free hemoglobin in rabbits.

Hoylaerts et al, *Thromb. Haemostas*, (Stuttgart), 49 (2), 109 (1983), and Ceustermans et al, *J. Biol. Chem.*, 257 (7), 3401 (1982), disclose covalent complexes of high affinity heparin fragments of low molecular weight and high affinity heparin with antithrombin-III having increased half-life compared with the uncomplexed heparin fragments and heparin and resulting in a 30-fold longer life time of Factor Xa inhibitory activity in plasma as compared with that of free intact heparin.

Bjork et al, *FEBS Letters*, 143 (1), 96 (1982), disclose covalent complexes formed by covalent attachment of antithrombin to high affinity heparin oligosaccharides, obtained by vitrous acid treatment of heparin, wherein the heparin oligosaccharide components have reactive aldehyde functions which form a Schiff's base with the amino group of any neighboring lysine residue of the protein.

Abuchowski et al, *J. Biol. Chem.*, 252 (11), 3578 and 3582 (1977), disclose the modification of proteins, specifically, bovine serum albumin and bovine liver catalase, by the covalent attachment thereto of nonimmunogenic methoxyproylene glycols of 1900 daltons (PEG-1900, Union Carbide Corp.) and 500 daltons (PEG-5000, Union Carbide Corp.) using cyanuric chloride (2,4,6-trichloro-s-triazine) as the coupling agent. The modified bovine serum albumin exhibited a blood circulating life in rabbits similar to native bovine serum albumin except that it was not removed from circulation by the eventual development of antibodies.

Also, the modified bovine serum albumin exhibited substantial changes in properties, such as solubility, electrophoretic mobility in acrylamide gel, ion exchange chromatography, and sedimentation, as compared with the unmodified protein. Rabbits were immunized by the intravenous administration of PEG-1900-catalase. The intravenous antiserum/antibodies did not yield detectable antibodies against PEG-1900-catalase or native catalase whereas the intramuscular antiserum contained antibodies to PEG-1900-catalase and native catalase. PEG-5000-catalase did not react with either antiserum. PEG-1900-catalase and PEG-5000-catalase retained 93% and 95%, respectively, of their enzymatic activity and PEG-5000-catalase resisted digestion by trypsin, chymotrypsin and a protease from *Streptoenyces griseus*. PEG-1500-catalase and PEG-5000-catalase exhibited enhanced circulating lives in the blood of acatalasemic mice during repetitive intravenous injection and no evidence was seen of an immune response to injections of the modified enzymes.

Ashihara et al, *Biochem. Biophys. Res. Commun.*, 83 (2), 385 (1978), disclose the modification of *E. coli* L-asparginase with activated polyethylene glycol (PEG-5000, PEG-1900, and PEG-750) to obtain products having varying levels of enzyme amino group substitution by means of covalent attachment of the polyethylene glycol to the enzyme amino groups. The modification of asparginase to 73 amino groups out of the total 92 amino groups in the molecule with PEG-5000 gave rise to a complete loss of the binding ability towards anti-asparginase serum from rabbits and retained the enzymatic activity (72) and hand versitivity against trypsin.

Koide et al, *FEBS Letters*, 143 (1), 73 (1982), disclose the preparation of polyethylene glycol-modified streptokinase by covalently attaching the glycol and the enzyme. The resulting modified streptokinase had a complete loss of antigenicity but had retention of its enzymatic activity.

O'Neill et al, *Biotechnol. Bioeng.*, 13, 319 (1971) disclose the covalent attachment of the enzyme, chymotrypsin, to dextran and to DEAE-cellulose using 2-amino-4,6-dichloro-s-triazine as the coupling agent. Determination of the activity of the preparations showed that chymotrypsin attached to the soluble substrate had a considerably higher activity towards both casein and anti-tyrosine ethyl ester than did chymotrypsin attached to DEAE-cellulose. Both of the conjugates had increased relative stability compared with native chymotrypsin as determined by incubating at 40° C. followed by assaying with acetyl-tyrosine ethyl ester (ATEE).

DESCRIPTION OF THE INVENTION

Summary of the Invention

This invention is the discovery that stable, water soluble, covalently attached complexes, also referred to as covalent conjugates, can be formed by the chemical coupling reaction of the blood plasma glycoprotein, alpha-l-proteinase inhibitor (abbreviated "$\alpha_1$PI") with an "activated" water soluble polymer. The "activated" water soluble polymer is a polysaccharide (or a carbohydrate) or a polyalkylene glycol produced by reacting the hydroxy groups thereof with a polyfunctional coupling compound having functional groups which are reactive with the polysaccharide or polyalkylene glycol pendant hydroxy groups to provide an intermediate which is reactive with $NH_2$ groups pendant to the protein, alpha-l-proteinase inhibitor.

Accordingly, in one aspect, this invention is a process for producing a covalently attached complex of alpha-l-proteinase inhibitor with an "activated" water soluble polymer. In another aspect, this invention is a covalent complex of alpha-l-proteinase inhibitor with an "activated" water soluble polymer produced by the process of the invention. In still another aspect, this invention is a pharmaceutical preparation of the covalent complex of alpha-l-proteinase inhibitor with an "activated" water soluble polymer and a pharmaceutically acceptable carrier. In yet another aspect, this invention is a method for treating pulmonary emphysema and respiratory distress syndrome by administering to a patient the covalent complex of alpha-l-proteinase inhibitor with an "activated" water soluble polymer. In a further aspect, this invention is the covalent complex of alpha-l-proteinase inhibitor with a water soluble polymer having bound thereto, by covalent attachment or by ionic association, an antioxidant catalase enzyme, and pharmaceutical preparations thereof.

DETAILED DESCRIPTION OF THE INVENTION

The process for producing the covalently attached complex of alpha-l-proteinase inhibitor with an "activated" water soluble polymer having hydroxy groups pendant to the polymer backbone, which hydroxy groups and amino groups pendant to alpha-l-proteinase inhibitor are chemically reactive with a polyfunctional coupling compound, comprises the steps of:

(a) contacting the water soluble polymer having hydroxy groups pendant to the polymer backbone, which hydroxy groups are chemically reactive with a polyfunctional coupling compound, with a polyfunctional coupling compound having functional groups which are reactive with said hydroxy groups in a chemical activation reaction to obtain an activated intermediate which is reactive with amino groups pendant to the protein, alpha-l-proteinase inhibitor; and (b) contacting the activated intermediate from step (a) with alpha-l-proteinase inhibitor in a chemical coupling reaction to effect covalent attachment and to thereby obtain a covalently attached complex of alpha-l-proteinase inhibitor with the water soluble polymer.

In another aspect, the process of the invention comprises the additional step of:

(c) isolating the covalently attached complex of alpha-l-proteinase inhibitor with the water soluble polymer obtained in step (b) from residual uncoupled alpha-l-proteinase inhibitor and water soluble polymer and undesirable compounds in the chemical coupling reaction mixture.

In a further aspect, the process of the invention comprises the addition of the antioxidant catalase enzyme (i) along with the alpha-l-proteinase inhibitor in step (b) above to provide a covalently attached complex of alpha-l-proteinase inhibitor, water soluble polymer and antioxidant catalase enzyme, or (ii) following step (b), above to provide an ionic association or complex of the covalently attached complex of alpha-l-proteinase inhibitor and water soluble polymer with the antioxidant catalase enzyme.

The water soluble polymer having hydroxy groups pendant to the polymer backbone which is used in the present invention may be selected from known water soluble and water solubilizable polymers including (a) dextran and dextran derivatives including dextran sulfate, p-aminoethyl cross-linked dextran, and carboxymethyl dextran; (b) cellulose and cellulose derivatives including methyl cellulose and carboxymethyl cellulose; (c) starch and dextrines derived from starch; (d) polyalkylene glycols and derivatives thereof including polyethylene glycols and methoxypolyethene glycols; (e) heparin; (f) polyvinyl alcohol; and (g) polyvinylpyrrolidone. Preferably, the water soluble polymer is selected from dextran and dextran derivatives, dextrine and dextrine derivatives, cellulose and cellulose derivatives, and polyethylene glycols and derivatives thereof. More preferably, the water soluble polymer is selected from dextran and dextran derivatives, dextrine and dextrine derivatives, and polyethylene glycols and derivatives thereof. Most preferably, the water soluble polymer is selected from dextran and dextran derivatives. In an especially preferred embodiment, the water soluble polymer is dextran.

The expression "activated" as applied to the water soluble polymer means that the water soluble polymer has been reacted with a polyfunctional coupling compound, which is reactive with the hydroxy groups pendant to the polymer backbone, to obtain an intermediate which is reactive, through the available functional group on the polyfunctional compound moiety or through a reactive intermediate functional group resulting from the chemical reaction of the polymer with the polyfunctional compound, with the amino groups pendant to the protein, alpha-l-proteinase inhibitor, which is believed to be attached through a lysine residue pendant to the protein.

The polyfunctional coupling compound which is used in the present invention may be selected from (a) a cyanogen halide wherein the halide is bromide, chloride or iodide; (b) cyanuric chloride (2,4,6-trichloro-s-1,3,5-triazine) and 2-amino-4,6-dichloro-s-1,3,5-triazine; (c) tolylene diisocyanate; (d) tolylene diisothiocyanate; and (e) 1,4-diaminobenzene in combination with CNBr. Preferably, the polyfunctional coupling compound is selected from a cyanogen halide and cyanuric chloride or the 2-amino derivative thereof. More preferably, the polyfunctional coupling compound is a cyanogen halide, most preferably, cyanogen bromide.

The chemical activation reaction may be carried out by known procedures such as those disclosed in the following:

Tam et al, *Proc. Natl. Acad. Sci. (U.S.A.)*, 73 (6), 2128 (1976), Marshall et al, *Arch. Biochem. Biophys.*, 167, 777 (1975) and *J. Biol. Chem.*, 251, 1081 (1976) and Christensen et al, *Int. Res. Commun. Syst. (Biochem.)*, 2, 1311 (1974) concerning CNBr activation of dextran; O'Neill et al *Biotechnol. Bioeng.*, 13, 319 (1971) concerning 2-amino-4,6-dichloro-s-1,3,5-triazine activation of dextran and DEAE-cellulose; Chaplin et al, *Biotechnol. Bioeng.*, 24, 2627 (1982) concerning CNBr and diaminobenzene activation of dextran; Abuchowski et al, *J. Biol. Chem.*, 252, 3578 and 3582 (1977) concerning cyanuric chloride activation of methoxypolyethylene glycols; Hoylaerts et al, *Thromb. Haemostas.* (Stuttgart), 49 (2), 109 (1983) and Ceustermans et al, *J. Biol. Chem.*, 257 (7), 3401 (1982) concerning the tolylene diisothiocyanate activation of heparin; and Rogers et al, *Biochem. Biophys. Res. Commun.*, 45, 662 (1971) concerning the tolylene diisocyanate activation of glycopeptide from fetuin.

In the especially preferred embodiment of the process of this invention, dextrans of average molecular weight ranging from about $1 \times 10^4$ to about $2 \times 10^6$ are activated using CNBr as described in Marshall et al, supra.

Alpha-l-proteinase inhibitor for use in the process of the invention may be produced by any of the several processes mentioned above. Alpha-l-proteinase inhibitor produced by intracellular recombinant DNA technology is also intended to be within the scope of the process according to this invention. Preferred processes to obtain $\alpha_1$PI are the processes described in Coan et al, U.S. Pat. No. 4,379,087 and in continuation-in-part thereof, U.S. Ser. No. 461,422 filed Jan. 27, 1983 concerning a method for separating $\alpha_1$PI from a blood plasma fraction, fraction IV-1, obtained by the Cohn ethanol fractionation technique (Cohn et al, *J. Chem. Soc.*, 68, 459 (1946) and U.S. Pat. No. 2,390,074) using a polycondensed polyglycol such as polyethylene glycol of molecular weight of about $2 \times 10^3$ to $1 \times 10^4$ under conditions which effect precipitation of unwanted proteins which are removed. The alpha-l-proteinase inhibitor is then separated from the remaining solution by contacting the solution with a suitable ion exchange medium and then eluting from he medium the alpha-l-proteinase inhibitor.

In the especially preferred embodiment of the process herein, the alpha-l-proteinase inhibitor is then contacted with the activated dextran by a modification of the method disclosed in Marshall et al, supra.

In the following description, emphasis is directed to the especially preferred process of the invention. Following the methods described in Marshall et al, *J. Biol. Chem.*, 251 (4), 1081 (1976), to a stirred aqueous solution of dextran in water adjusted to pH of about 9.0 to 13.0, preferably 10.0 to 12.0, there is added cyanogen bromide to obtain an activated dextran intermediate. Usually, about 1 to 2 parts of dextran are used per 0.05 to 1 part of cyanogen bromide. Preferably, about 1 to 2 parts of dextran are used per 0.2 to 0.5 part of cyanogen bromide.

The activation step is carried out at a temperature of from about 2° to 35° C., preferably about 5° to 20° C., for a reaction period of about 5–60 minutes, preferably about 15–30 minutes. Unreacted cyanogen bromide is then removed by dialysis.

The solution of the activated dextran intermediate, adjusted to a pH of about 8–10.5, preferably about 9.0–9.8, is then mixed with a solution containing about 1 to 2 parts of purified alpha-l-proteinase inhibitor ($\alpha_1$PT) per 10 to 30 parts of dextran in the activated dextran intermediate, the residual active groups being neutralized with glycine.

The temperature of this coupling reaction is about 2°–35° C., preferably about 5°–20° C., and the coupling reaction time is about 0.5–24 hours, preferably about 3–12 hours.

The coupling reaction product mixture containing the covalently bound alpha-l-proteinase inhibitor-dextran complex may then be processed to put it in condition for use. Generally, the product mixture is concentrated to reduce its water content by conventional means. Also, if desired although not required, uncoupled $\alpha_1$PI and dextran remaining in solution in the product mixture may then be removed by conventional means, for example, dialysis, diafiltration, chromatography, etc. The resulting concentrates containing the covalently bound alpha-l-proteinase inhibitor-dextran complex can be formulated into pharmaceutical preparations for therapeutic use. The resulting covalently bound alpha-l-proteinase inhibitor-dextran complex concentrate and pharmaceutical compositions containing the complex may be sterilized by conventional means, sterile-filtered, and treated to render them non-hepatitis infective. As used herein, the expression "sterilize" is meant to embrace those means which will inactivate or destroy microorganisms, including viruses and especially hepatitis virus, so as to reduce or eliminate the microorganisms to render them non-infective.

Pharmaceutical preparations comprising the covalently bound, or covalently chemically coupled, alpha-l-proteinase inhibitor-dextran complex may be sterilized to render the preparations non-microorganism and non-hepatitis infective by conventional, known procedures, for example, heat treatment, chemical treatment using for example, β-propiolactone or chloroform or Tween ® 80 to name but a few representative chemical viral inactivating agents, ultraviolet radiation treatment and colloidal silica. For example, the preparations, in wet or dry state, may be heated at temperatures of about 60°–85° for a period of several minutes to several days. Optionally, the heat treatment procedure may be advantageously carried out in the presence of a heat stabilizing amount of at least one heat stabilizing agent. Suitable stabilizing agents include citrate ions, nonpolar anions with molecular weights greater than 80, sugars, reduced sugars, and amino acids. Examples of suitable nonpolar anions include salts of carboxylates, hydroxycarboxylates and amino acids such as sodium or potassium caprylate, caprate, oleate, laurate, valerate, acetylphenylalaninate, acetyleucinate, and acetyltryptophanate. Examples of suitable sugars include glucose, sucrose and maltose to name but a few, and examples of suitable reduced sugars include erythritol and mannitol. Examples of suitable amino acids include lysine, glysine, proline and glutamic acid to name but a few. By way of example without limitation, suitable conventional known sterilization processes include those disclosed in U.S. Pat. Nos. 3,041,242, 3,057,781, 3,227,626, 4,061,735, 4,137,307, 4,297,344, 2,705,230, 2,897,123, 3,284,301, 3,454,929, 4,379,085 and 4,370,264, and European Patent Publication No. 0058993, and in references disclosed in the patents.

In this respect the concentrates may be treated to reduce hepatitis infectivity by, for example, pasteurization, i.e., heating at a temperature and for a time, such as, for example, at about 60° C. or more for a period up to about 10 hours, sufficient to render the alpha-l-proteinase inhibitor-dextran covalent complex hepatitis non-infective. To stabilize the alpha-l-proteinase inhibitor-dextran covalent complex during this heat treatment a source of citrate ions is added in an amount sufficient to stabilize the alpha-l-proteinase inhibitor-dextran covalent complex during heating. Generally, if about 20 mg of total protein is present in the alpha-l-proteinase inhibitor-dextran covalent complex concentrate, then the solution is made about 0.25–0.5M in citrate ion. The pH of the mixture during this heating step should preferably be about 6.0–7.0.

To achieve maximum stabilization of alpha-l-proteinase inhibitor-dextran covalent complex during heating it is desirable to use a carbohydrate as the stabilization agent either alone or with sodium citrate. For this purpose one may use as the carbohydrate a mono-, di-, and trisaccharide such as arabinose, glucose, galactose, maltose, fructose, fibose, mannose, rhammose, sucrose, etc., or a sugar alcohol such as sorbitol and mannitol, etc., in an amount of about 0.5–2.4 g/ml of alpha-l-proteinase inhibitor-dextran covalent complex solution.

The covalent alpha-l-proteinase inhibitor-dextran complex product and concentrates thereof can be formulated into pharmaceutical preparations containing the complex and a pharmaceutically acceptable carrier. The term "pharmaceutical preparation" is intended in a broad sense herein to include preparations used for therapeutic purposes, for reagent purposes, for diagnostic purposes, for tissue culture purposes, and so forth. The pharmaceutical preparation intended for therapeutic use should contain a pharmaceutically acceptable and useful concentration of the complex to provide a therapeutically effective amount of the complex, i.e., that amount necessary for preventative or curative health measures. If the pharmaceutical preparation is to be employed as a reagent, then it should contain reagent amounts of complex. Similarly, when used in tissue culture or as a culture medium the pharmaceutical preparation should contain an amount of complex sufficient to obtain the desired growth.

It is a characteristic of compositions comprising the alpha-l-proteinase inhibitor-dextran complex prepared in accordance with the present invention that they contain the complex in pharmaceutically useful amounts to provide therapeutically effective amounts.

To prepare them for intravenous administration the compositions are constituted usually in water containing physiologically compatible substances such as sodium chloride, glycine, sugar and the like in physiologically compatible concentrations and having a buffered pH compatible with physiological conditions. Generally, guidelines for intravenously administered compositions are established by governmental regulations.

The following examples are illustrative of but a few embodiments of the invention described above and are not to be construed as limiting in scope. All parts and percentages are by weight and all temperatures are in degrees Celsius unless otherwise indicated.

MATERIALS AND METHODS

Cohn Fraction IV-1, the source of alpha-l-proteinase inhibitor, was obtained by means of the Cohn fractionation scheme mentioned above in Cohn et al, *J. Amer. Chem. Soc.*, 68, 459 (1946). Purification of alpha-l-proteinase inhibitor was initiated by sequential fractionation with polyethylene glycol (PEG 4000 ®, Union Carbide Corporation) at pH 5.0–5.5, as described in U.S. Pat. No. 4,379,087 and copending continuation-in-part thereof U.S. Ser. No. 461,922 filed Jan. 27, 1983, both of which are owned by the assignee of the present application, followed by treatment by means of ion exchange chromatography techniques on DEAE Sepharose CL-6B using a conventional phosphate buffer (0.1M sodium phosphates, pH 6.5) as the eluent. The protein was determined to be at least 90% pure by means of sodium dodecyl sulfate polyacrylamide gel electrophoresis (SDS-PAGE) techniques as described by Weber et al, *J. Biol. Chem.*, 244, 4406 (1969).

Cyanogen bromide was obtained from Aldrich Chemical Co.

Dextran of average molecular weight 17,700 and 10,300 daltons was obtained from Sigma Chemical Co. (St. Louis, MO).

Porcine pancreatic elastase type III and chromogenic substrate N-succinyl-L-anlanyl-L-alanyl-L-alanyl-p-nitroanilide (SA3pNA) were obtained from Sigma Chemicals Co. (St. Louis, MO). Hydrolysis of the chromogenic substrate by the elastase liberates p-nitroaniline which gives a yellow color whose absorbance is measurable spectrophotometrically (Model 1084 UV Spectrophotometer, Gilford Instruments, Oberlin, OH) at 405 nm. Alpha-l-proteinase inhibitor inhibits this hydrolysis reaction and the extent of elastase inhibition is proportional to the amount of alpha-l-proteinase inhibitor present.

Comparisons of the linear changes of absorbance with time both in the presence and in the absence of sample alpha-l-proteinase inhibitor and of sample alpha-l-proteinase inhibitor-dextran covalent complex were made. The amount of inhibitor was then calculated based on the known molecular weights of the elastase and alpha-l-proteinase inhibitor, on the known 1:1 stoichrometry, and on the known amount of elastase used. A pool of normal human plasma (>1000 donors) was used as the standard and assigned a value of 1 $\mu$/ml of $\alpha_1$PI.

Antiserum (rabbit anti-human) to alpha-l-proteinase inhibitor was obtained from Miles Laboratories (Elkhart, IN). Comparison to purified alpha-l-proteinase inhibitor showed that 1 unit of alpha-l-proteinase inhibitor activity was equivalent to 1.3 mg.

Association constants ($k_{assoc}$) between the enzyme (E) and the inhibitor (I) were determined as follows: 25 $\mu$l each of equimolar amounts of the enzyme and the inhibitor were incubated at 37° C. with 1950 $\mu$l of buffer (0.05M TRIS, 0.15M NaCl, pH 7.4) (TRIS ® is tris(hydroxymethyl)amino methane, supplied by Sigma, St. Louis, Mo.) to obtain a resultant concentration of $3.37 \times 10^{-7}$. At various times, a 200 $\mu$l aliquot of the enzyme-inhibitor solution was added to 780 $\mu$l buffer and 20 $\mu$l substrate (SA3pNA) (60 mM) and the hydrolysis rate followed in the temperature controlled (37° C.) cuvette with a recorder (Model 6051, Gilford Instruments, Oberlin, Ohio) attachment. During hydrolysis no further enzyme-inhibitor association was assumed (5 fold dilution compared to preincubation) and the initial reaction rate (v) was indicative of the free enzyme (E) present at the end of the respective preincubation times. Enzyme inhibitor association is represented as:

$$E + I \underset{k_{dissoc}}{\overset{k_{assoc}}{\rightleftarrows}} EI \quad (1)$$

for $k_{dissoc} \simeq 0$ and equimolar concentrations of E and I we get $$-dE/dt = k_{assoc}E^2 \quad (2)$$

With initial conditions t=0, E=Eo (all free enzyme) equation (2) integrates to $$1/E - 1/E_o = k_{assoc}t \quad (3)$$

By defining half life of the reaction $t_{0.5}$ to be at $E = 0.5E_o$ we get $$t_{0.5} = 1/k_{assoc}E_o \quad (4)$$

Exclusion Chromatography:

High performance liquid chromatography (HPLC) runs were made with a Varian Spherogel TSK 3000 column (Varian Instruments, Palo Alto, CA) of size 7.5×300 mm. The buffer used was 0.05M phosphate, 0.1M KCl (pH 6.8) at a flow rate of 1 ml/min; 60 $\mu$l of the sample was applied. A Hitachi model 100-300 (Allen Scientific, Berkeley, CA) UV (280 nm) director with a Hewlett Packard (Hewlett Packard, Palo Alto, CA) Model 3388 computing integrator was used to identify the protein peaks. A Bio Rad (Richmond, CA) molecular weight standard was run for the purpose of calibration.

Studies Related to Heating and Oxidation:

Alpha-1-proteinase inhibitor and its dextran conjugates, with and without added beef liver catalase as antioxidant, were heated in closed tubes at 60±0.2° C. The tubes were preheated and due to large mass difference the samples reached the bath temperature in less than 60 seconds. At designated time intervals samples were withdrawn and instantaneously cooled down (by ice bath) to room temperature prior to assay.

Hydrogen peroxide (30% solution, Sigma Chemicals) was used as the oxidation agent to investigate the effect of 0–28 mM $H_2O_2$ on the recovery of elastase inhibitory capacity (EIC) following incubation at 37° C. for 1 hour.

EXAMPLE 1

Preparation of covalently bound dextran-alpha-1-proteinase inhibitor complex 1 g dextran (average mol. wt. 17,700, Sigma Chemicals, industrial grade) was covalently coupled to 209 mg of purified human alpha-1-proteinase inhibitor prepared from Cohn Fraction IV-1 (Elastase inhibitory capacity/mg total protein=1.5) by first dissolving the dextran in 100 ml of water at pH 10.7 and 20° C. and then adding to the solution 0.4 g of cyanogen bromide. The pH of the resulting solution of dextran and cyanogen bromide was adjusted to 10.7 and maintained at 20° C. for 40 minutes. This solution was dialyzed against pH 9.6 water (pH adjusted with 1M $Na_2CO_3$) for 3 hours at 20° C. to remove spent reactants. Purified alpha-1-proteinase inhibitor, 209 mg, was added to the solution. The pH of the resulting mixture was adjusted to, and maintained at, 9.6 and the temperature held at 5° C. for 18 hours to permit the coupling reaction to proceed. At the end of the coupling step the solution was dialyzed against water at pH 7.6 (pH adjusted with 1M $Ha_2CO_3$) for 3 hours at 20° C. 0.7 g glycine was added to the dextran-alpha-1-proteinase inhibitor solution, the final pH of the solution was 7.10. The properties of the resulting alpha-1-proteinase inhibitor-dextran covalent complex are summarized in Table I.

EXAMPLES 2–5

By following substantially the procedure described in Example 1 above except that the starting amount of purified alpha-1-proteinase inhibitor (per gram of dextran) was changed from 209 mg in Example 1 to 100 mg, 20 mg, 100 mg, 20 mg in Examples 2–5, respectively, there were prepared the additional alpha-1-proteinase inhibitor-dextran complexes of Examples 2–5 whose properties are summarized in Table I.

BIOLOGICAL EVALUATION

TABLE I

| | Alpha-1-Proteinase Inhibitor Recovery Across Covalent Coupling | | |
|---|---|---|---|
| Example No. | Dextran Mol. Wt. | Moles Dextran / Moles $\alpha_1$PI | % EIC Recovered |
| 2 | 17,700 | 0.0681 | 52.42% |
| 3 | 17,700 | 0.3404 | 32.14% |
| 4 | 10,300 | 0.117 | 28.8% |
| 5 | 10,300 | 0.585 | 18.4% |

Table 1 shows the activity, expressed in terms of the elastase inhibitory capacity (EIC), of the alpha-1-proteinase inhibitor-dextran complexes according to the invention having varying molar ratios. Recovery of EIC appears inversely proportional to the dextran/molar ratio. This observation is consistent with the hypotheses that increased amino group substitution results in changed conformation of the reactive center resulting in decreased biological activity. Subsequent experiments were all carried out with 10,300 mol. wt. dextran.

Table II shows the results of precipitation reactions of alpha-1-proteinase inhibitor and its dextran (mol. wt. 10,3000) conjugates with rabbit antiserum to the unmodified protein. For unmodified alpha-1-proteinase inhibitor, only 0.092 μg of protein was sufficient to obtain a strong precipitin reaction. For the 0.117 moles dextran/mole alpha-1-proteinase inhibitor conjugate, 14.5 μg of alpha-1-proteinase inhibitor was needed to elicit a similar response—a very significant increase of antigen concentration. For the 0.585 moles dextran/mole alpha-1-proteinase inhibitor conjugate increase of antigen concentration up to 29.0 μg was not sufficient to obtain a strong precipitin reaction with the antiserum. These results suggest that increased dextran attachment via amino group substitution results in masking of the antigenic determinants of the native protein molecule.

TABLE II

| Precipitin Reactions of Alpha-1-Proteinase Inhibitor and Conjugates with Rabbit Antiserum (dil. 1:2) to Unmodified Protein | | |
|---|---|---|
| Sample | Antigen Conc. (μg) | Precipitin Reaction |
| Unmodified alpha-1-proteinase inhibitor | 0.092 | Strong |
| 0.117 Moles Dextran / Mole $\alpha_1$PI (Ex. No. 4) | 14.5 | Strong |
| 0.585 Moles Dextran / Moles $\alpha_1$PI (Ex. No. 5) | 1.95 | Weak |
| | 29.0 | Weak |

Table III shows the calculation of the association constants ($k_{assoc}$) between the inhibitors and the enzyme according to equation (4). The initial reaction rate (Δ absorbance/5 minutes) depicts the hydrolysis rate of the substrate by the free enzyme present following the respective preincubation time. Initial reaction rate, in the absence of the inhibitor, was determined and the time required for this rate to decrease to half of its original value ($t_{0.5}$) was calculated. Equation (4) was subsequently used to calculate $k_{assoc}$ for each of the 3 cases.

Beatty et al, *J. Biol. Chem.*, 255, 3931 (1980), reported the $k_{assoc}$ value between native alpha-1-proteinase inhibitor and porcine elastase (each at $1.4 \times 10^{-8}M$) to be $1 \times 10^5 M^{-1} sec.^{-1}$. Our value ($1.85 \times 10^5 M^{-1} sec.^{-1}$) for the native protein is reasonably close to that of Beatty et al considering the variabilities in source/purity of the protein, molarities of the protein and the enzyme and the alpha-1-proteinase inhibitor standard used for the assays.

TABLE III

| | Rate Constant for the Association Between the Enzyme and the Inhibitor | | | |
|---|---|---|---|---|
| Sample | Preincubation Time (Secs.) | Initial Reac. Rate Δ Absorbance / 5 Minutes | $t_{0.5}$ (secs.) | $(M^{-1}Sec^{-1})$ |
| Control, No $\alpha_1$PI | — | 0.890 | | |
| Native $\alpha_1$PI | 15 | 0.460 | | |
| | 30 | 0.310 | 16.17 | $1.85 \times 10^5$ |

TABLE III-continued

| Sample | | Preincubation Time (Secs.) | Initial Reac. Rate Δ Absorbance 5 Minutes | $t_{0.5}$ (secs.) | $(M^{-1}Sec^{-1})$ |
|---|---|---|---|---|---|
| | | 60 | 0.173 | | |
| | | 65 | 0.170 | | |
| | | 90 | 0.128 | | |
| 0.117 | Moles Dextran / Mole $\alpha_1$PI (Ex. No. 4) | 20 | 0.450 | 21.49 | $1.41 \times 10^5$ |
| | | 45 | 0.285 | | |
| | | 75 | 0.195 | | |
| | | 120 | 0.130 | | |
| 0.585 | Moles Dextran / Mole $\alpha_1$PI (Ex. No. 5) | 25 | 0.495 | 34.67 | $8.56 \times 10^4$ |
| | | 65 | 0.285 | | |
| | | 100 | 0.205 | | |
| | | 145 | 0.135 | | |

A progressive decrease of $k_{assoc}$ is noted with increasing dextran concentrations. Conformational changes in the protein molecule and steric hindrances are probably involved during the formation of the covalent conjugates resulting in decreased association rates with the enzyme.

In order to investigate the pH stability of these preparations, experimental samples were adjusted to pH 3.0 with controls at pH 7.40 and incubated for 24 hours at +5° C. Following this, pH was adjusted back up to 7.40 for the experimental samples and EIC assays carried out immediately. Samples were further incubated for 24 hours at +5° C. and reassayed. In Table IV the results are presented as percent of control at each assay point.

TABLE IV pH Stability (pH 3.0) of the Native Protein and its Conjugates

| | Recovery of EIC as % of Control After Adjustment to pH 7.4 | |
|---|---|---|
| Sample | Immediate | Incubation Time 24 hrs. (5° C.) |
| Native $\alpha_1$PI | 41 | 66 |
| Conjugate w 0.117 Moles Dextran / Mole $\alpha_1$PI (Ex. No. 4) | 68 | 81 |
| Conjugate w 0.585 Moles Dextran / Mole $\alpha_1$PI (Ex. No. 5) | 55 | 93 |

The inactivation of alpha-1-proteinase inhibitor at acid pH is believed to be attributable to formation of molecular aggregates. Reincubation at neutral pH results in recovery of EIC activity which is time dependent as depicted in Table IV. The conjugates show improved recovery compared to the native protein.

Figure 1:
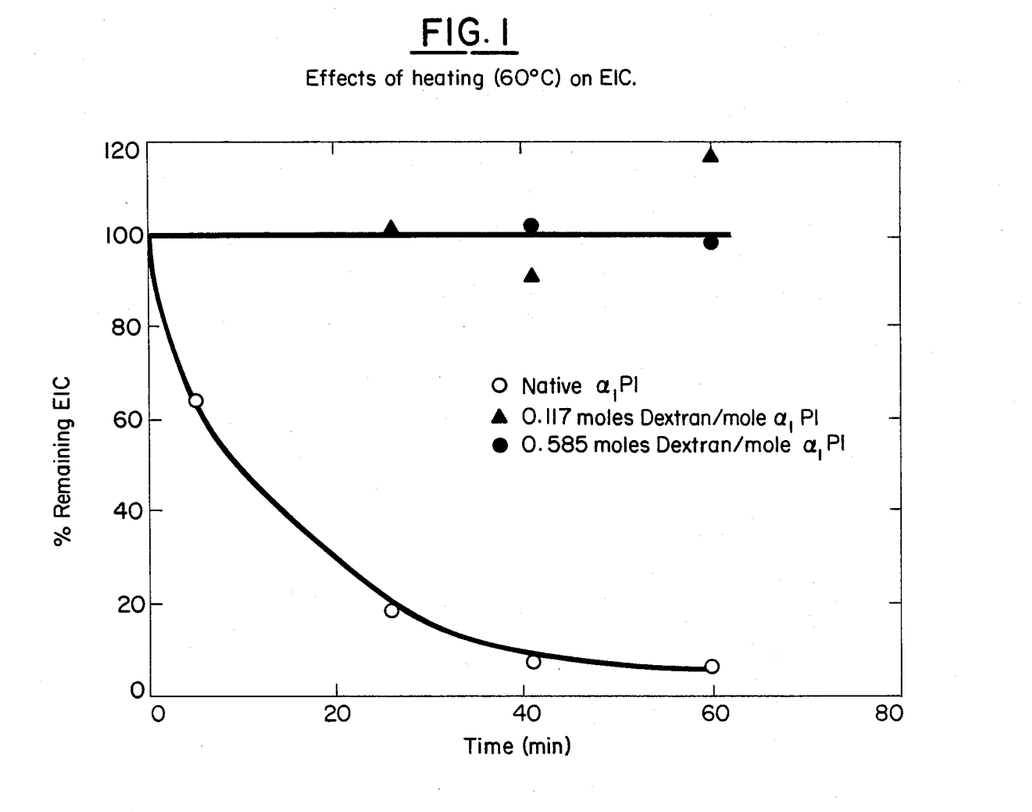

Effects of heating at 60° C. of these samples are shown in FIG. 1. A significant difference here is observed between the native protein and its conjugates. Within 60 minutes, native alpha-1-proteinase inhibitor loses >90% of its initial activity whereas the conjugates do not show any significant reduction of EIC.

Figure 2:
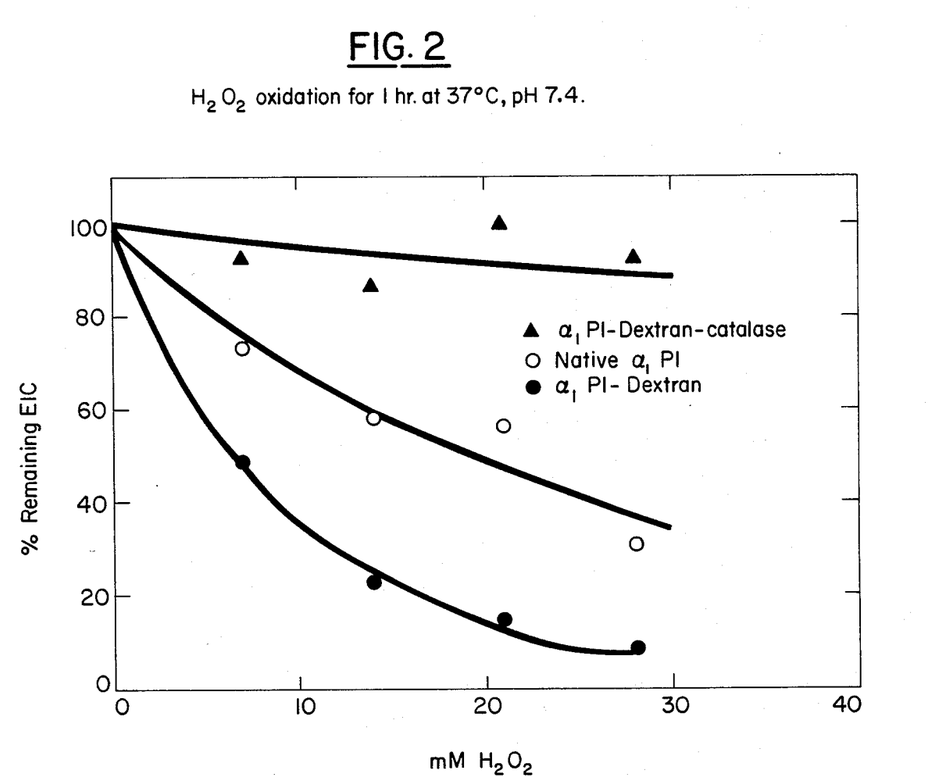

Oxidative inactivation of alpha-1-proteinase inhibitor has been related to its reactive center methionine according to Johnson et al, *J. Biol. Chem.*, 254, 4022 (1979). Hydrogen perioxide and other agents (periodate, dimethyl sulfoxide, chloromine-T, N-chlorosuccinamide) have been used to oxidize methionine to inactive methionine sulfoxide. FIG. 2 (oxidation at pH 7.4) depicts the effects of various concentrations of $H_2O_2$ on the samples. Oxidation at pH 6.4 showed similar trends in the data. It is apparent from FIG. 2 that only the alpha-1-proteinase inhibitor-dextran-catalase conjugate ($\alpha_1$PI-dextran conjugate further complexed with bovine liver catalase wherein 100 mg of catalase per g of dextran was added during the coupling reaction of $\alpha_1$PI with dextran) showed resistance to oxidative degradation by $H_2O_2$. Native alpha-1-proteinase inhibitor as well as its dextran conjugate showed significant progressive loss of EIC with increasing $H_2O_2$ concentration. It was experimentally determined that physical addition of equivalent amounts of catalase would also inhibit $H_2O_2$ oxidation. The advantage of covalently bound catalase might be that in an in vivo system close proximity of alpha-1-proteinase inhibitor and catalase may be of importance. It is to be understood that any antioxidant enzyme may be used, e.g. catalase or an equivalent enzyme such as superoxide dismutase.

Figure 3:
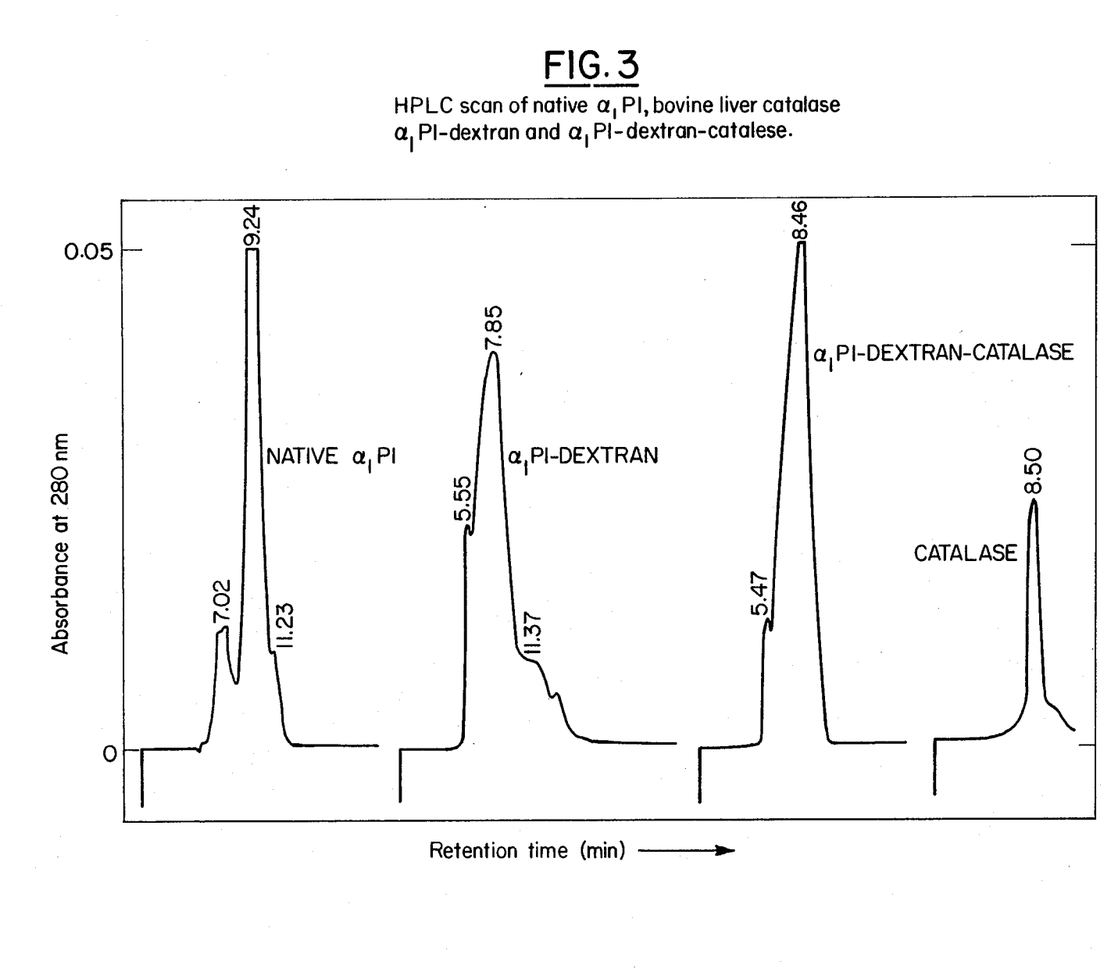

HPLC scans of the various samples are shown in FIG. 3. As expected, the conjugates show a heterogenous molecular species distribution, the void volume fraction (retention time ~5.5 minutes) being <5% of total protein. On the other end of the spectrum no significant portion of the protein had retention times >11.71 minutes, the retention time corresponding to that of horse myoglobin (m.w. 7,000). The HPLC results were confirmed with SDS-PAGE which also determined the presence of higher molecular weight components.

Accordingly, the data set forth and described above illustrate the advantages of the covalent alpha-1-proteinase inhibitor complex with a water soluble polymer, particularly, such advantages including improved heat and pH stability and reduced antigenicity. Dextran, a polysaccharride which has been widely used as a blood plasma volume extender, has been selected as the water soluble polymer of choice because of its ready availability and the convenience by which it may undergo activation with the simple coupling agent, cyanogen bromide.

In contrast to native alpha-1-proteinase inhibitor, the alpha-1-proteinase inhibitor produced by intracellular recombinant DNA technology is non-glycosylated. The process of this invention may be advantageously employed to obtain a glycosylated form, that is, a chemically, covalently coupled alpha-1-proteinase inhibitor-dextran conjugate, or the r-DNA-produced alpha-1-proteinase inhibitor which would be expected to possess the characteristics of improved heat and pH stability and reduced antigenicity possessed by the conjugate produced from native (that is, plasma) alpha-1-proteinase inhibitor.

What is claimed is:

1. A process for producing a covalently attached complex of alpha-1-proteinase inhibitor with a water soluble polymer having hydroxy groups pendant to the polymer backbone, which hydroxy groups and amino groups pendant to alpha-1-proteinase inhibitor are chemically reactive with a polyfunctional coupling compound, comprising the steps of:
   (a) contacting the water soluble polymer having hydroxy groups pendant to the polymer backbone, which hydroxy groups are chemically reactive with a polyfunctional coupling compound, with a polyfunctional coupling compound having functional groups which are reactive with said hydroxy groups in a chemical activation reaction to obtain an activated intermediate which is reactive with amino groups pendant to the protein, alpha-1-proteinase inhibitor; and
   (b) contacting the activated intermediate from step (a) with alpha-1-proteinase inhibitor in a chemical coupling reaction to effect covalent attachment and to thereby obtain a covalently attached complex of alpha-1-proteinase inhibitor with the water soluble polymer.

2. A process according to claim 1 including the further step of:
   (c) isolating the covalently attached complex of alpha-1-proteinase inhibitor with the water soluble polymer obtained in step (b) from residual uncoupled alpha-1-proteinase inhibitor and water soluble polymer undesirable compounds in the chemical coupling reaction mixture.

3. A process according to claim 1 wherein the water soluble polymer having hydroxy groups pendant to the polymer backbone, which hydroxy groups are chemically reactive with a polyfunctional coupling compound, is selected from (a) dextran and dextran derivatives including dextran sulphate, p-aminoethyl cross-linked dextran, and carboxymethyl dextran; (b) cellulose and cellulose derivatives including methyl cellulose and carboxymethyl cellulose; (c) starch and dextrines derived from starch and dextrine derivatives; (d) polyalkylene glycols and derivatives thereof including polyethylene glycols and methoxypolyethene glycols; (e) heparin; (f) polyvinyl alcohol; and (g) polyvinylpyrrolidone.

4. A process according to claim 3 wherein the polyfunctional coupling compound is selected from (a) a cyanogen halide wherein the halide is bromide, chloride or iodide; (b) cyanuric chloride (2,4,6-trichloro-s-1,3,5-triazine) and 2-amino-4,6-dichloro-s-1,3,5-triazine; (c) tolylene diisocyanate; (d) tolylene diisothiocyanate; and (e) 1,4-diaminobenzene combined with cyanogen bromide.

5. A process according to claim 4 including the further step of:
   (c) isolating the covalently attached complex of alpha-1-proteinase inhibitor with the water soluble polymer obtained in step (b) from residual uncoupled alpha-1-proteinase inhibitor and water soluble polymer undesirable compounds in the chemical coupling reaction mixture by means, effective to separate the complex from residual uncomplexed alpha-1-proteinase inhibitor and water soluble polymer and undesirable compounds in the chemical coupling reaction mixture obtained in step (b), selected from ion exchange chromatography, affinity chromatography, dialysis, ultrafiltration and electrophoresis techniques.

6. A process according to claim 4 comprising the steps of:
   (a) contacting a water soluble polymer having hydroxy groups pendant to the polymer backbone, which hydroxy groups are chemically reactive with a polyfunctional coupling compound, selected from (i) dextran and dextran derivatives including dextran sulphate, p-aminoethyl cross-linked dextran, and carboxymethyl dextran, (ii) dextrines and dextrine derivatives, (iii) cellulose and cellulose derivatives including methyl cellulose and carboxymethyl cellulose, and (iv) polyethylene glycols and derivatives thereof including methoxypolyethylene glycols, with a polyfunctional coupling compound selected from (i) cyanogen bromide and (ii) cyanuric chloride (2,4,6-trichloro-s-1,3,5-triazine) and 2-amino-4,6-dichloro-s-1,3,5-triazine in a chemical activation reaction to obtain an activated intermediate which is reactive with amino groups pendant to the protein, alpha-1-proteinase inhibitor; and
   (b) contacting the activated intermediate from step (a) with alpha-1-proteinase inhibitor in a chemical coupling reaction to effect covalent attachment and to thereby obtain a covalently attached complex of alpha-1-proteinase inhibitor with the water soluble polymer.

7. A process according to claim 6 including the further step of:
   (c) isolating the covalently attached complex of alpha-1-proteinase inhibitor with the water soluble polymer obtained in step (b) from residual uncoupled alpha-1-proteinase inhibitor, water soluble polymer and undesirable compounds in the chemical coupling reaction mixture by ion exchange chromatography and ultrafiltration techniques.

8. A process according to claim 6 wherein the water soluble polymer is selected from dextran and dextran derivatives and the polyfunctional coupling compound is cyanogen bromide.

9. A covalently attached complex of alpha-1-proteinase inhibitor with a water soluble polymer produced by the process of claim 1.

10. A covalently attached complex of alpha-1-proteinase inhibitor with a water soluble polymer produced by the process of claim 5.

11. A covalently attached complex of alpha-1-proteinase inhibitor with a water soluble polymer produced by the process of claim 6.

12. A covalently attached complex of alpha-1-proteinase inhibitor with a water soluble polymer produced by the process of claim 8.

13. A pharmaceutical preparation comprising a pharmaceutically acceptable and useful concentration of the complex of claim 9 and a pharmaceutically acceptable carrier.

14. A pharmaceutical preparation comprising a pharmaceutically acceptable and useful concentration of the complex of claim 10 and a pharmaceutically acceptable carrier.

15. A pharmaceutical preparation comprising a pharmaceutically acceptable and useful concentration of the complex of claim 11 and a pharmaceutically acceptable carrier.

16. A pharmaceutical preparation comprising a pharmaceutically acceptable and useful concentration of the complex of claim 12 and a pharmaceutically acceptable carrier.

17. A sterilized covalently attached complex of alpha-1-proteinase inhibitor with a water soluble polymer produced by sterilizing the complex produced by the process of claim 1 to render the complex non-viral infective.

18. A sterilized covalently attached complex of alpha-1-proteinase inhibitor with a water soluble polymer produced by sterilizing the complex produced by the process of claim 5 to render the complex non-viral infective.

19. A sterilized covalently attached complex of alpha-1-proteinase inhibitor with a water soluble polymer produced by sterilizing the complex produced by the process of claim 6 to render the complex non-viral infective.

20. A sterilized covalently attached complex of alpha-1-proteinase inhibitor with a water soluble polymer produced by sterilizing the complex produced by the process of claim 8.

21. A sterilized pharmaceutical preparation produced by sterilizing the pharmaceutical preparation of claim 13 to render the preparation non-viral infective.

22. A sterilized pharmaceutical preparation produced by sterilizing the pharmaceutical preparation of claim 14 to render the preparation non-viral infective.

23. A sterilized pharmaceutical preparation produced by sterilizing the pharmaceutical preparation of claim 15 to render the preparation non-viral infective.

24. A sterilized pharmaceutical preparation produced by sterilizing the pharmaceutical preparation of claim 16 to render the preparation non-viral infective.

25. A method for treating pulmonary emphysema and respiratory distress syndrome which comprises administering to a patient the pharmaceutical preparation of claim 13.

26. A method for treating pulmonary emphysema and respiratory distress syndrome which comprises administering to a patient the pharmaceutical preparation of claim 14.

27. A method for treating pulmonary emphysema and respiratory distress syndrome which comprises administering to a patient the pharmaceutical preparation of claim 15.

28. A method for treating pulmonary emphysema and respiratory distress syndrome which comprises administering to a patient the pharmaceutical preparation of claim 16.

29. A method for treating pulmonary emphysema and respiratory distress syndrome which comprises administering to a patient the pharmaceutical preparation of claim 21.

30. A method for treating pulmonary emphysema and respiratory distress syndrome which comprises administering to a patient the pharmaceutical preparation of claim 22.

31. A method for treating pulmonary emphysema and respiratory distress syndrome which comprises administering to a patient the pharmaceutical preparation of claim 23.

32. A method for treating pulmonary emphysema and respiratory distress syndrome which comprises administering to a patient the pharmaceutical preparation of claim 24.

33. A process according to claim 1 comprising the further addition of about 1.0 to 300 mg of antioxidant catalase enzyme per g of dextran (i) in step (b) along with the alpha-1-proteinase inhibitor to obtain a covalently attached complex of alpha-1-proteinase inhibitor and water insoluble polymer and catalase, or (ii) following step (b) to obtain an ionic association of the covalently attached complex of alpha-1-proteinase inhibitor and the water soluble polymer with catalase.

34. A process according to claim 2 comprising the further addition of about 1.0 to 300 mg of antioxidant catalase enzyme per g of dextran (i) in step (b) along with the alpha-1-proteinase inhibitor to obtain a covalently attached complex of alpha-1-proteinase inhibitor and water insoluble polymer and catalase, or (ii) following step (b) to obtain an ionic association of the covalently attached complex of alpha-1-proteinase inhibitor and the water soluble polymer with catalase.

35. A process according to claim 6 comprising the further addition of about 1.0 to 300 mg of antioxidant catalase enzyme per g of dextran (i) in step (b) along with the alpha-1-proteinase inhibitor to obtain a covalently attached complex of alpha-1-proteinase inhibitor and water insoluble polymer and catalase, or (ii) following step (b) to obtain an ionic association of the covalently attached complex of alpha-1-proteinase inhibitor and the water soluble polymer with catalase.

36. A process according to claim 7 comprising the further addition of about 1.0 to 300 mg of antioxidant catalase enzyme per g of dextran (i) in step (b) along with the alpha-1-proteinase inhibitor to obtain a covalently attached complex of alpha-1-proteinase inhibitor and water insoluble polymer and catalase, or (ii) following step (b) to obtain an ionic association of the covalently attached complex of alpha-1-proteinase inhibitor and the water soluble polymer with catalase.

37. A process according to claim 8 comprising the further addition of about 100 mg of antioxidant beef liver catalase enzyme per g of dextran (i) in step (b) along with the alpha-1-proteinase inhibitor to obtain a covalently attached complex of alpha-1-proteinase inhibitor and water insoluble polymer and catalase, or (ii) following step (b) to obtain an ionic association of the covalently attached complex of alpha-1-proteinase inhibitor and the water soluble polymer with catalase.

38. A covalently attached complex of alpha-1-proteinase inhibitor, a water soluble polymer, and antioxidant catalase produced according to claim 33.

39. A covalently attached complex of alpha-1-proteinase inhibitor, a water soluble polymer, and antioxidant catalase produced according to claim 34.

40. A covalently attached complex of alpha-1-proteinase inhibitor, a water soluble polymer, and antioxidant catalase produced according to claim 35.

41. A covalently attached complex of alpha-1-proteinase inhibitor, a water soluble polymer, and antioxidant catalase produced according to claim 36.

42. A covalently attached complex of alpha-1-proteinase inhibitor, a water soluble polymer, and antioxidant catalase produced according to claim 37.

43. A pharmaceutical preparation comprising a pharmaceutically acceptable and useful concentration of the complex of claim 38 and a pharmaceutically acceptable carrier.

44. A pharmaceutical preparation comprising a pharmaceutically acceptable and useful concentration of the complex of claim 39 and a pharmaceutically acceptable carrier.

45. A pharmaceutical preparation comprising a pharmaceutically acceptable and useful concentration of the complex of claim 42 and a pharmaceutically acceptable carrier.

* * * * *